(12) United States Patent
Randolph et al.

(10) Patent No.: US 6,319,521 B1
(45) Date of Patent: Nov. 20, 2001

(54) MICROPARTICLES OF LACTIDE-CO-GLYCOLIDE COPOLYMERS AND METHODS OF MAKING AND USING THE SAME

(75) Inventors: Theodore W. Randolph, Niwot; Corinne Lengsfeld, Denver, both of CO (US); Richard Frank Falk, III, Bend, OR (US)

(73) Assignee: University Technology Corporation, Boulder, CO (US)

( * ) Notice: Subject to any disclaimer, the term of this patent is extended or adjusted under 35 U.S.C. 154(b) by 0 days.

(21) Appl. No.: 09/501,003

(22) Filed: Feb. 9, 2000

Related U.S. Application Data
(60) Provisional application No. 60/119,547, filed on Feb. 10, 1999, now abandoned.

(51) Int. Cl.[7] ........................................... A61K 9/14
(52) U.S. Cl. ........................... 424/489; 424/484; 424/486
(58) Field of Search ............................... 424/45, 426, 484, 424/489, 497

(56) References Cited

U.S. PATENT DOCUMENTS

| | | | |
|---|---|---|---|
| 5,232,707 | * | 8/1993 | Lokensgard ........................ 424/490 |
| 6,126,919 | * | 10/2000 | Stefely et al. ........................ 424/45 |

* cited by examiner

*Primary Examiner*—Thurman K. Page
*Assistant Examiner*—Liliana Di Nola-Baron
(74) *Attorney, Agent, or Firm*—Medlen & Carroll, LLP

(57) ABSTRACT

The present invention relates to the formation of microparticles from copolymers during a process involving precipitation with compressed antisolvents. The family of suitable copolymers have a semi-crystalline structure that above their glass transition temperature retain sufficient crystalline strength to form microparticles. The invention also provides systems comprising the microparticles encapsulated with a desired compound for the controlled release of the compound over a predetermined period of time.

8 Claims, 8 Drawing Sheets

(a)

(b)

MICROPARTICLES OF LACTIDE-CO-GLYCOLIDE COPOLYMERS AND METHODS OF MAKING AND USING THE SAME

This application claims priority benefit to U.S. Provisional Patent Application Ser. No. 60/119,547, filed Feb. 10, 1999, now abandoned.

FIELD OF THE INVENTION

The present invention relates to the use of lactide-co-glycolide copolymers to form microparticles using precipitation by compressed antisolvents.

BACKGROUND OF THE INVENTION

The technique of precipitation by compressed antisolvents (PCA) has been used to manufacture linear-homopolymer microparticles to encapsulate a variety of materials for the controlled release of the encapsulated materials. Encapsulation of materials, particularly pharmaceutical drugs, into biodegradable polymers using PCA is attractive because of high encapsulation efficiency (Falk et al, *J. Controlled Release*, 44:77–85 (1997)), low residual solvent levels, low processing temperatures (Falk & Randolph, *Pharmaceutical Research*, 15(8):1233–1237 (1998)), and the production of micron sized particles (Randolph et al, *Biotech. Progress*, 9:429–435 (1993); Dixon et al., *AIChE J.*, 39(1):127–139 (1993)).

However, the use of PCA at times produces certain undesirable results. For example, linear-homopolymers, such as poly(lactide), encapsulated microparticles release the encapsulated materials over several months, which is a relatively long period of time. Such long release times are particularly undesirable for many pharmaceutical delivery applications, because of potential adverse patient reactions. In addition, the high solubility of supercritical carbon dioxide ($CO_2$), which enables the rapid extraction of solvent from the polymer during PCA, also causes large quantities of $CO_2$ to diffuse into the polymer. Acting as a diluent, $CO_2$ lowers the glass transition temperature ($T_g$) of the polymer. Polymers susceptible to a suppression of $T_g$ below the operating temperature of the PCA system may form agglomerated particles or thin films during precipitation.

The study of $CO_2$ effects on polymers is not new. $T_g$ suppression was originally observed in the creep rates recorded for poly(carbonate) pipes pressurized with $CO_2$ (Hojo & Findley, *Polymer Engr. Science*, 13:255–265 (1973)). Eventually this behavior led to new production methods for polymer foams, the extraction of low molecular weight compounds from polymers, and the impregnation of polymers with chemical additives (Wissinger & Paulaitis, *Industrial & Engr. Chem. Res.*, 30:842–851 (1991)). Experimental measurements of $T_g$ suppression by $CO_2$ include observing the relaxation of mechanical properties (Wang et al., *J. Polymer Sci. Part B: Polymer Physics*, 20(6):1371–84 (1982)), differential scanning calorimetry (Chiou et al., *J. Applied Polymer Sci.*, 30:2633–2642 (1985)), and creep compliance (Condo & Johnston, *J. Polymer Sci: Part B: Polymer Physics*, 32:523–533 (1994)). Thermodynamic models using lattice fluid theory and the Gibbs-Di Marzio criterion predict glass transition temperatures as a function of pressure remarkably well (Condo et al., *Macromolecules*, 25(23)6119–6127 (1992); Kalosiros & Paulaitis, *Chem. Engr. Sci.*, 49(5):659–668 (1994)). Together, models and experiments led to the classification of four fundamental polymer behaviors, and the understanding that the $T_g$ of a polymer or copolymer at a particular pressure depends on the pure polymer $T_g$ and the solubility of $CO_2$ within the polymer. Thus research to date on viable polymers for PCA has been limited to measuring or predicting a polymer's glass transition temperature after interaction with compressed carbon dioxide. As a result, previous theory deemed all polymers with glass transition temperatures below the operating conditions of the PCA system as unusable.

Bodmeier et al., *Pharmaceutical Research*, 12(8):1211–1217 (1995) reported some interesting observations while determining suitable polymers for PCA. Bodmeier et al. based the compatibility of a polymer on the degree of swelling observed in compressed $CO_2$. From the six polymers investigated, they reported the highly crystalline and the semi-crystalline polymers were generally unaffected by high pressure $CO_2$ exposure, while all the amorphous polymers agglomerated under similar conditions.

Poly(lactide-co-glycolide) is a common biodegradable pharmaceutical polymer. The copolymer has been extensively used for suture material and, in the last decade, has been explored as a potential drug release medium. However, the PCA technique was believed to be unsuitable for the copolymer because compressed carbon dixoide severely affects the mechanical properties of the copolymer and prevents formation of microparticles.

Accordingly, a need exists for methods of using lactide-co-glycolide copolymers in PCA to form microparticles. The present invention satisfies this need and provides related advantages.

SUMMARY OF THE INVENTION

The invention generally relates to novel methods for making poly(lactide-co-glycolide) microparticles and using the microparticles as delivery vehicles for the controlled release of a variety of compounds, including pharmacueticals. The invention is based on the discovery of a family of copolymers that can be successfully manufactured into microparticles above their glass transition as long as sufficient crystalline structure exists to maintain suitable mechanical strength.

Accordingly, the methods for making the microparticles in a precipitation by compressed antisolvent (PCA) process are generally accomplished by first obtaining any "semi-crystalline copolymer" having a semi-crystalline structure, such as poly(lactide-co-glycolide), that above its glass transition temperature will retain sufficient degree of its crystalline strength to form microparticles. Thereafter, the copolymer is exposed to a compressed antisolvent to form the semi-crystalline copolymeric microparticles. The antisolvent used in the methods is preferably carbon dioxide, and more preferably carbon dioxide in a supercritical or liquid state.

The critical crystallinity of suitable copolymers (below which insufficient crystalline structure exists to form microparticles during PCA) depends on a variety of factors including, for example, the molecular weight of the copolymer, the operating temperature of the PCA process, the glass transition temperature of the copolymer and the mechanical strength of the copolymer. Preferably, the critical crystallinity of the copolymer is in the range of about 10% to about 15%, and more preferably about 12% particularly when the molecular weight of the copolymer is about 100 kDa.

The invention also relates to the microparticles composed of any copolymers designed so that the critical crystallinity is achieved to facilitate production by the above methods, including the microparticles produced by the above methods. Examples of suitable semi-crystalline copolymers to form microparticles include polystyrene and polyethers, as well as the lacide-co-glycolide copolymers.

The invention further provides systems for the controlled release of various compounds that are encapsulated in the semi-crystalline copolymeric microparticles and to methods of using the systems to control the release of the compounds to a target environment over a predetermined period of time. The controlled release of the compounds is accomplished by varying the ratio of the copolymer components. Depending on the intended use, the ratio can range from 100:0 to 0:100 of the individual components. For example, a ratio of 50:50 to 30:70 of poly(lactide) to poly(glycolide) is particularly useful for the controlled release of pharmaceutical agents when a shorter release time is desired. Thus, the release time using the present family of copolymers can range from weeks to months by varying this ratio.

DETAILED DESCRIPTION OF THE INVENTION

Figure 1:
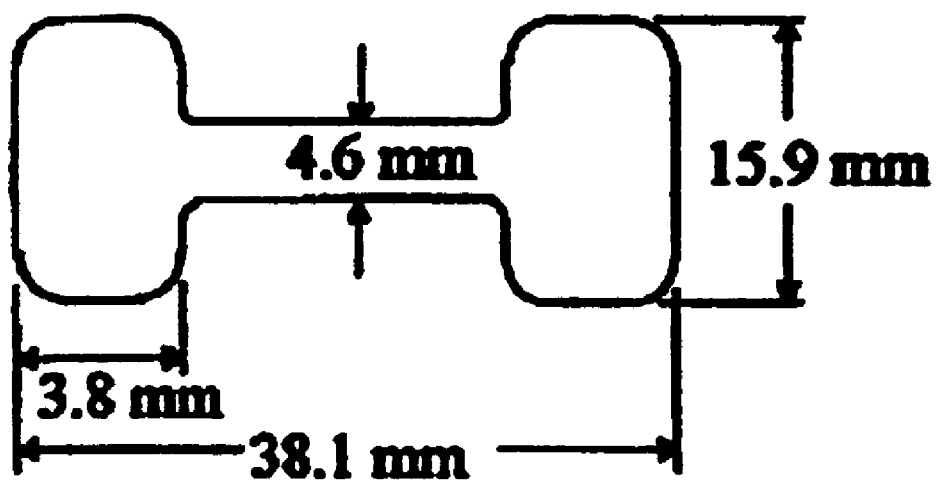
FIG. 1 shows a standard tensile specimen.

The present invention is based on the discovery of a family of semi-crystalline copolymers capable of forming microparticles using the PCA technique. It was previously believed that the properties of such lactide-co-glycolide copolymers were ineffective in resisting the solvent capability of compressed carbon dioxide and, therefore, were not suitable for manufacturing microparticles using the PCA technique. However, as noted above, it has now been discovered that such copolymers can be successfully manufactured into microparticles above their glass transition as long as sufficient crystalline structure exists to maintain suitable mechanical strength.

The lactide molecule in the lactide-co-glycolide copolymer chain occurs in two isometric forms: l and d. If the copolymer has approximately equal portions of randomly positioned l and d isomers, the copolymer will have an amorphous (non-crystalline) structure and will form a film rather than microparticles during PCA. However, if the lactide-co-glycolide copolymer is constructed of glycolide blocks and l-lactide or d-lactide blocks, adequate crystallinity can be maintained over a range of composition ratios to form microparticles. Similar blocks can be constructed for other semi-crystalline copolymers.

A critical crystallinity exists below which the benefits conferred by the strong disperse phase cannot offset the plasticizing effects of carbon dixoide in the amorphous phase. For example, poly(l-lactide-co-glycolide) copolymers are semi-crystalline at l-lactide mole percents smaller than 30% and larger than 75%. Such semi-crystalline copolymers have crystalline regions as well as amorphous regions.

The mechanical properties of the amorphous regions are highly temperature dependent at temperatures above the glass transition temperature of the particular polymer, and less temperature dependent at temperatures below the glass transition temperature. As the temperature increases above the glass transition temperature, the amorphous regions lose their mechanical integrity and strength. Thus, until the present discovery, it was believed that polymers with glass transition temperatures below the operating conditions of the PCA system were unsuitable for manufacturing microparticles for use as a controlled release medium.

However, it has now been found that the success of a polymer in forming microparticles during PCA results from the existence of strong moduli, particularly Young's modulus, in the presence of compressed $CO_2$. The Young's modulus of a material is nearly invariant with crystalline structure below its glass transition, but above the glass transition the behavior of the modulus greatly depends on the volume fraction of the crystalline phase. Thus, as crystallinity increases, the less Young's modulus decreases. This results from the fact that the glass transition temperature of polymers is dependent upon the quantity of $CO_2$ incorporated into the structure. Accordingly, $CO_2$ solubility is reduced by using copolymers having greater crystalline structure.

In one embodiment, the present invention provides methods for making poly(lactide-co-glycolide) microparticles using the PCA technique and to the microparticles made by such methods. The methods are generally accomplished by first obtaining a semi-crystalline copolymer. Thereafter, the semi-crystalline copolymer is exposed to a compressed antisolvent to form the semi-crystalline copolymeric microparticles. The PCA technique is well known and is described, for example, in Falk et al, *J. Controlled Release*, 44:77–85 (1997), Falk & Randolph, *Pharmaceutical Research*, 15(8):1233–1237 (1998), Randolph et al, *Biotech. Progress*, 9:429–435 (1993), and Dixon et al., *AIChE J.*, 39(1):127–139 (1993), all incorporated herein by reference. The antisolvent used in the methods is preferably carbon dioxide, and more preferably carbon dioxide in a supercritical or liquid state.

As noted previously, the critical crystallinity of suitable semi-crystalline copolymers depends on a variety of factors including, for example, the molecular weight of the copolymer, the operating temperature of the PCA process, the glass transition temperature of the copolymer and the mechanical strength of the copolymer as measured by the existence of a strong moduli, particularly Young's modulus, in the presence of the compressed antisolvent. For example, as the molecular weight of the copolymer decreases, the critical crystallinity will need to increase. Similarly, even if the $T_g$ of a particular polymer is above, but close to, the operating temperature of the PCA process, the critical crystallinity needs to be higher compared with a polymer having a $T_g$ much greater than the operating temperature. Those skilled in the art can readily predict the critical crystallinity of a particular copolymer. Preferably, the critical crystallinity of most lactide-co-glycolide copolymers is in the range of about 10% to about 15%, and more preferably about 12% particularly when the molecular weight of the copolymer is about 100 kDa.

The invention further provides systems for the controlled release of various compounds that are encapsulated in the semi-crystalline copolymeric microparticles. The discovery of a family of lactide-co-glycolide copolymers capable for forming microparticles during PCA opens an entirely new area of copolymers with controllable release properties.

The systems of the present invention are comprised of a quantity of a desired compound encapsulated into the microparticles produced according to the above methods. The components of the copolymer are in a ratio suitable for the controlled release of the compound over a predetermined period of time. The controlled release of compounds is accomplished by varying the ratio of the copolymer components. Depending on the intended use, the ratio can range from 100:0 to 0:100 of the individual components. For example, a ratio ranging from about 50:50 to about 30:70 of poly(lactide) to poly(glycolide) is particularly useful for the controlled release of pharmaceutical agents when a shorter release time is desired. For other applications in which a longer release time is desired other ratios can be used, for example, 65:35, 75:25, 85:15, 25:75, and 20:80 of poly (lactide) to poly(glycolide). Thus, the release time using the present family of copolymers can range from weeks to months by varying this ratio.

Any compound that can be encapsulated or otherwise incorporated (generally referred to herein as "encapsulated") into the semi-crystalline copolymeric microparticles without losing its desired activity can be used in the present systems. Suitable compounds include, for example, chemicals, drugs, and pharmaceutical agents including proteins, peptides, nucleic acids. Therapeutic agents such as chemotherapeutics, other toxins, vitamins, minerals and the like can also be delivered in the present systems. Suitable compounds can also be used as markers for diagnostic purposes when tracking the markers over a period of time is desired. For cell culture or other in vitro applications, suitable compounds include for example useful cell culture additives, chemicals and in vitro test compounds. Those skilled in the art can readily identify other suitable compounds without undue experimentation.

The present invention also provides methods of using the microparticle systems for the controlled release of the encapsulated compounds into a target environment over a predetermined period of time. The target environment can be related to in vitro or in vivo applications. For in vitro applications, the microparticle-encapsulated compounds can be delivered by any suitable means known to those skilled in the art depending on the application. For example, the microparticles can be added to cell culture media before or after adding the cells to the media.

For in vivo applications, the methods are generally accomplished by administering the semi-crystalline copolymeric microparticles encapsulated with a desired compound to a patient in need of the compound. The amount, i.e. dose, of the compound to be delivered by the microparticles and the mode of administration depend on a variety of factors and can be readily determined by those skilled in the art. Such factors include the compounds to be administered, the condition to be treated or diagnosed, the condition and age of the patient, the target location, and for dosing, the mode of administration, which can include oral, pulmonary, injection or other parenteral administration.

The following Examples are intended to illustrate, but not limit, the present invention. In the Examples, the following chemicals were used as received: poly(dl-lactide-co-glycolide)(50:50, 65:35, 75:25, 85:15) and poly(glycolide) [$T_g$=35–40° C.](Sigma); poly(l-lactide) Resomer L206 and poly(d,l-lactide) Resomer R206 [$T_g$=55–60° C.] (Boehringer Ingelhem); poly(d,l-lactide-co-glycolide) (85:15)(Purac America; methylene chloride ($CH_2Cl_2$) (Fisher); and the molecular probe 16-doxyl-stearic acid (Aldrich).

To provide accuracy between pressure measurements made on two separate systems, the pressure transducers were calibrated from 0 to 60 MPa using a Heise gauge with accuracy to ±0.01 Mpa.

EXAMPLE 1

Creep Experiments

Standard tensile specimens (FIG. 1) were fashioned in a stainless steel mold enclosed by glass slides by heating the polymer to temperatures slightly above their melting temperature. When the polymer filled the mold, the specimen was cooled slowly by turning off the heat source. After removal from the mold, polymer specimens were suspended by one end inside an optically accessible pressure chamber. Suspension from the thick portion ensured failure occurred away from locations of point loading.

The chamber was initially charged with carbon dioxide to a pressure of 4 MPa and a temperature of 35° C. The pressure was controlled using an ISCO compressed gas pump in the constant pressure mode and measured using a digital pressure transducer (Omega). Chamber temperatures were maintained using an air bath surrounding the test chamber. An Omega thermocouple and temperature control unit controlled air temperature.

The system equilibrated for 1 hour at the initial pressure and temperature setting, upon which the pressure was raised 0.5 MPa every hour thereafter. Changes in surface color/texture and gauge length were monitored. The test concluded when the specimen broke or elongated substantially within one hour. Generally, no elongation occurred at any pressure other than the failure pressure. One hour increments were assumed to provide sufficient time for the $CO_2$ to equilibrate within the 1 mm thick sample because one hour is the same order suggested for $CO_2$ equilibration within a similarly sized poly(methyl methacrylate) sample at 25° C. and 6.7 MPa by Berens and Huvard, *Supercritical Fluid Science and Technology*, ACS Symposium Series 406, 204–223 (Johnston & Penffinger, eds. 1989).

EXAMPLE 2

EPR Spectrometry

Electron Paramagnetic Resonance (EPR) experiments were performed on a Bruker ESP300 EPR spectrometer. A high-pressure EPR cell was constructed out of a thick walled, closed end quartz tube with the open end affixed to a 6.35-mm stainless steel tube for connection to the pressurizing system. Pressure in the cell was controlled with a hand operated syringe pump (High Pressure Equipment) and measured with a digital pressure transducer (Omega). The carbon dioxide that feed the syringe pump passed through a scrubber to remove traces of oxygen (Labclear). Temperatures in the cell were measured with a thermocouple, and the cell was thermostated to ±0.1° C. using a liquid nitrogen boil-off and an Eurotherm temperature controller.

A 6 wt % solution of polymer in $CH_2Cl_2$ with approximately 100 µM concentration of the stable free radical spin probe 16-doxyl-stearic acid was injected into the EPR high pressure cell (pressure tests on 16-doxyl-stearic acid up to 8 MPa showed no signs of extraction by supercritical carbon dioxide). At this molarity the probe molecule will not affect the polymer properties and experiences negligible spin exchange. The $CH_2Cl_2$ was evaporated in a warm air bath resulting in the deposit of a thin film of polymer and probe on the inside surface of the EPR high pressure cell. To ensure removal of any residual $CH_2Cl_2$ from the polymer deposit, the EPR cell was place under vacuum. Results were collected from a single cell more than once to observe any shift in pressure of the transitional behavior that may have resulted from residual $CH_2Cl_2$. Methylene chloride is extremely soluble in $CO_2$ and, therefore, was completely removed from the polymer film after a single pressurized run. Using a $CH_2Cl_2$ solution ensures that the deposited polymer physically entraps the probe molecule. As a result, local polymer properties govern the probe molecule's behavior.

Measurements were made using two different methods: (i) a conventional $1^{st}$ harmonic spectrum extrema separation technique, and (ii) a saturation transfer phase sensitive detection scheme sensitive to slow motion which maps the peak ratio of the $2^{nd}$ harmonic spectra. For the first technique, a conventional first harmonic X-band EPR spectrum was recorded using a modulation amplitude of 1-G, a 100 kHz modulation frequency, a time constant of 20.48 ms, and a microwave power of 10 mW. Each recorded spectrum was the average of three 34-s, 200-G scans. In the second technique, saturation transfer, the out of phase second harmonic of X-band EPR spectrum, was recorded using a modulation amplitude of 10-G, a 50 kHz modulation frequency, a time constant of 5.12 ms, and microwave power of 100 mW. To ensure no bleed through existed, phase shifts were adjusted to null a conventional at 1-G modulation amplitude and 100 kHz modulation. Each recorded spectrum was the average of three 21-s, 150-G scans.

For each coated cell, the pressure was raised in 0.5 MPa increments. To insure that the system had equilibrated after each change in pressure, spectra were recorded until no difference between subsequent spectra could be discerned (because the polymer films were so thin this occurred within the first two recorded spectra).

Figure 2:
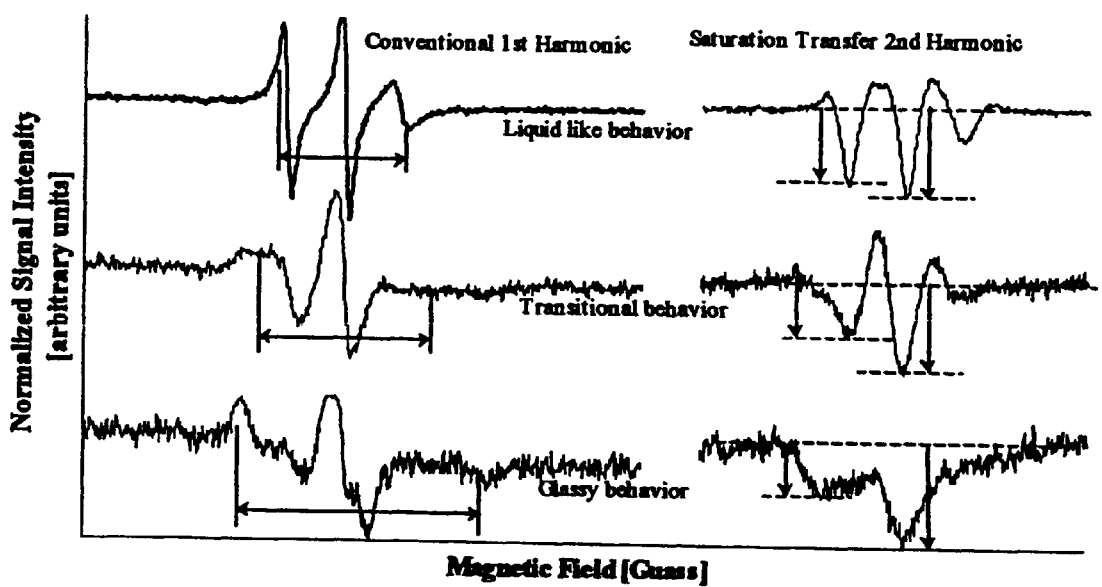
FIG. 2 presents both convention $1^{st}$ harmonic and saturation transfer $2^{nd}$ harmonic EPR spectra collected for 16-doxyl-stearic acid trapped in 65:36 poly(d,l-lactide-co-glycolide) in the presence of $CO_2$ at 35° C. EPR cell pressure starting from the top and working down; 5.5 MPa, 3 MPa and atmospheric conditions.
Figure 3:
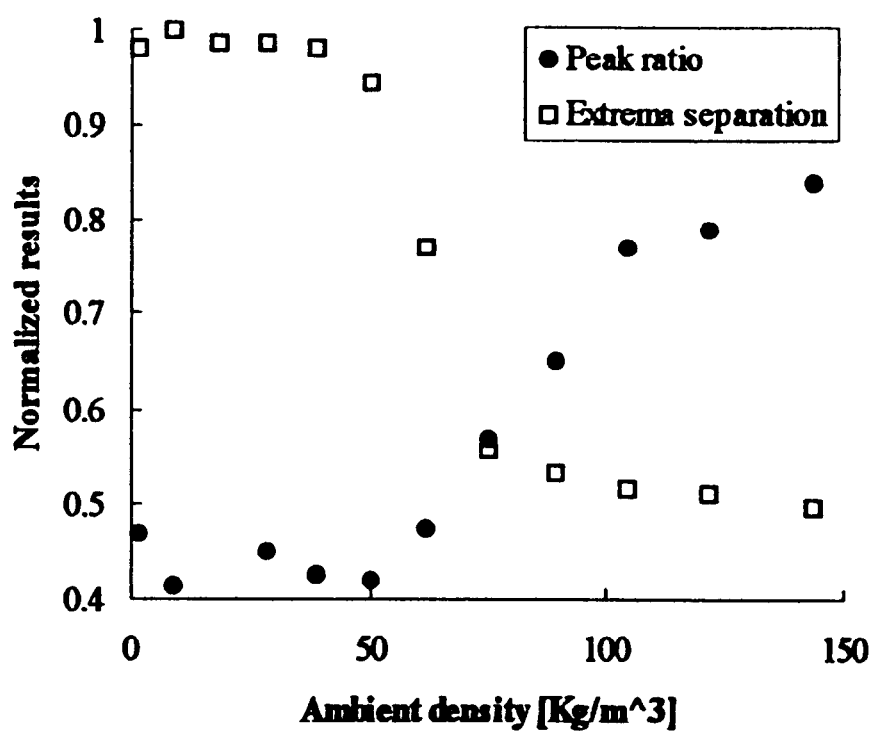
FIG. 3 shows the variation of extrema separation and peak ratio versus $CO_2$ ambient density for 16-doxyl-stearic acid trapped in 65:35 poly(d,l-lactide-co-glycolide).

The extrema separation was measured from the conventional spectra. Extrema separation is the magnetic field separation between the maximum of the low intensity line peak and the minimum of the high intensity line peak in the first derivative signal from the EPR absorption spectrum (FIG. 2). The use of extrema separation to determine glass transition temperatures for amorphous polymers using spin probes from the nitroxide family has been reported in Keinath, *International Symposium on Order in the Amorphous "State of Polymers"* $17^{th}$ Symposium, pp. 187–219 (1985). In the three-line nitroxide signal, the separation distance remains long (approximately 65 gauss) and unchanged, while the polymer is glassy. The separation decreases rapidly as the polymer transitions to a more liquid-like (or plastic) behavior. Once the polymer is beyond this transitional region, the separation becomes constant near 35 gauss (FIG. 3). Keinath noticed the glass transition temperature occurred when the spectral width was 50 gauss for a wide variety of polymers. For this study, $CO_2$ induced glass transition pressure was determined based on this 50 gauss extrema separation because 16-doxyl-stearic acid is a member of the nitroxide family and the separation magnitudes were similar to those observed by Keinath.

This extrema separation method worked well even in the semi-crystalline polymers because a large portion of the probe molecules were trapped in amorphous regions of the maximum 40% crystalline polymer film. As the local viscosity drops in the amorphous regions, the resulting EPR signal should be significantly stronger than the probe molecules trapped in regions dominated by crystalline structure.

In saturation transfer, only the portion of the signal that arises from saturation transfer rates were selected. This selection was done using phase-sensitive detection where the modulation frequency was 50 kHz, while the phase-sensitive detection remained at 100 kHz. For this method, the greatest sensitivity was found to be out-of-phase with respect to the second harmonic of the modulation. Once satisfactory spectra are obtained, it has previously been shown that following the growth or decay of an intermediate peak with respect to a peak on a turning point is a good indication of how the local viscosity around the probe molecule changes as reported in Thomas et al., *J. Chem. Phys..*, 65(8):3006–3024 (1976). Thomas et al. determined that this ratio was linearly proportional to the ratio of sample temperature to local viscosity (T/η). For a nitroxide probe, the slope of low intensity line in the conventional spectra undergoes the most significant change of the three-line signal during the transition from a glassy polymer to a more plastic behavior. Furthermore, the low intensity line remain fairly constant upon the completion of the glass transition. Therefore, this study monitored the relative peak height between the low and intermediate negative signals from second harmonic saturation transfer spectra (FIG. 2). The ratio is small and constant in the glassy region and rapidly changes to a near unity and constant value in the fully plastic region (FIG. 3). The inflection point from this transition is considered the glass transition pressure induced by compressed carbon dioxide.

The two techniques result in similar glass transition pressures. From the 65:35 poly(d,l-lactide-co-glycolide) data presented in FIG. 3, the glass transition pressure from the extrema separation technique was found to be 3.0 MPa ($CO_2$ density=60 kg/m$^3$), while the saturation transfer method yields 3.9 MPa (84 kg/m$^3$). This was the poorest agreement between the two techniques observed in this study. In general, the transition points agreed within approximately ±0.2 MPa (±5 kg/m$^3$) and the saturation transfer method consistently measured a higher transition value. The glass transition pressures presented in the results are an average of the two methods.

EXAMPLE 3

X-ray Diffraction

X-ray diffraction was performed on a Rigaku powder x-ray diffraction instrument at 80 mA and 40 kV. Scans were conducted from 5° to 40° at a step width of 0.05° and a rate of 2 seconds per step. 45-mg polymer powder samples were prepared on a glass slide by gently compressing all the powder onto a strip 12 mm×25 mm. Although the strip was slightly smaller than the beam width, this method provides a thick layer of polymer that the beam does not penetrate completely. Partial beam penetration of a sample helps make the comparison of signal magnitude from various samples less dependent on sample quantity and more statistically reliable. The spectral contribution resulting from the exposed portion of the glass slide is far from the region of interest and can be assumed negligible.

EXAMPLE 4

Dynamic Mechanical Analyzer

Representative crystalline and amorphous Young's moduli were obtained using a Perkin Elmer Dynamic Mechanical Analyzer (DMA model 7e). The analyzer was run in the three point bend mode with a static load of 50 mN and a dynamic load of 10 mN. Amplitude control was set to 8 $\mu$m displacement and tension control to 120%. The forcing amplitude was monitored over the entire operating conditions and found to remain nearly constant. The forcing frequency was 1 Hz. Rectangular amorphous polymer samples were approximately 3 mm wide, 1.3 mm thick and 12 to 15 mm long. The support holder had pressure points 10 mm apart. Sample moduli were observed from thermal scans from temperatures well below the glass transition (0° C.) to a temperature 20 degrees above the glass transition (80° C.) at a heating rate of 3° C./min. Representative crystalline modulus was determined from the measurements far below the glass transition temperature where temperature dependence is minor. The amorphous modulus was determined from the measurements far above the glass transition where once again temperature dependence has become minor.

EXAMPLE 5

Differential Scanning Calorimeter

X-ray diffraction cyrstallinities were verified using a Perkin Elmer Differential Scanning Calorimeter (DSC model 7) with a Nesslab RTE- 111 chiller set to 0° C. and a nitrogen purge. Thermal scans of 2-mg powder samples were conducted twice. The first scan heated the sample at 10° C./min. This step improves the polymer contact with the pan and relaxes any material strains that may exist. In the second scan, the samples were heated at 10° C./min from 25° C. to 220° C. Crystallinity was determined from subtracting the enthalpy of recrystalized (area under the normalized recrystalization exotherm) from the enthalpy of ftision (area under the normalized melting endotherm) divided by the enthalpy of a 100% sample (93.6 J/g[16]).

EXAMPLE 6

Results and Discussion

Figure 4:
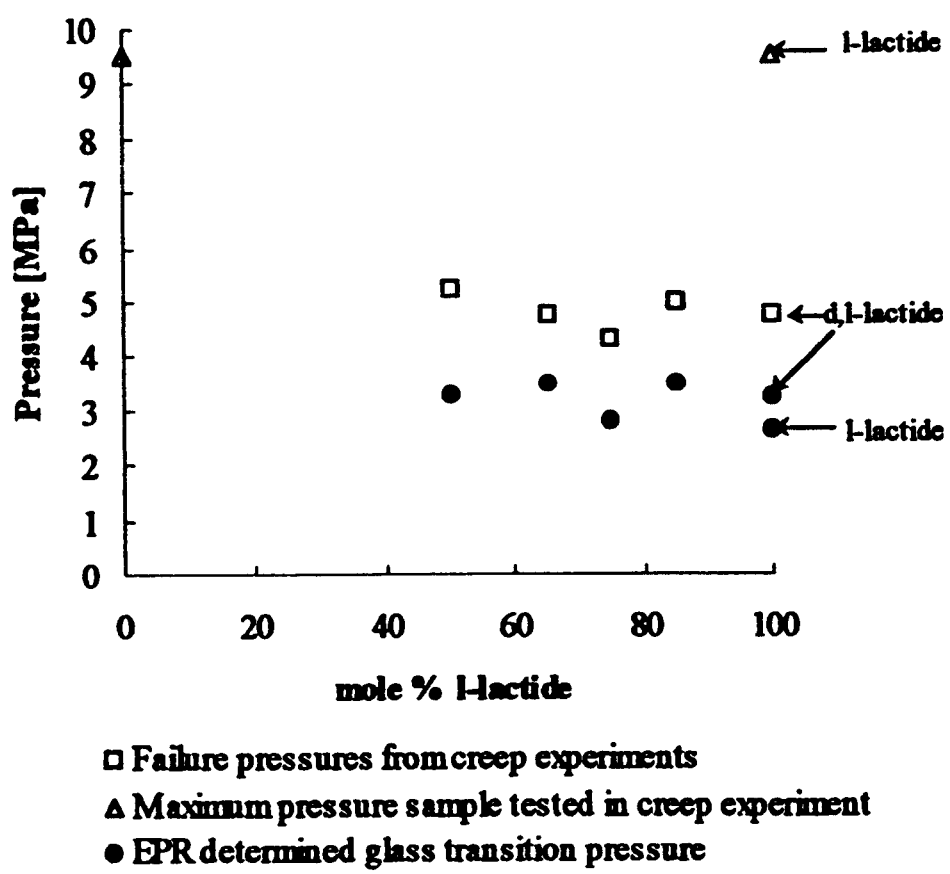
FIG. 4 shows the failure and glass transition pressure comparison for various poly(lactide)-poly(glycolide) copolymers and homopolymers.

EPR and mechanical creep experiments were conducted on polymer samples ranging from pure poly(glycolide) to pure poly(lactide) and several of their co-polymers. The range of co-polymer composition for the amorphous results is required to decipher if deviations in EPR and creep data result from crystallinity or chemical composition. FIG. 4 shows the transition pressures at 35° C. for both the creep and EPR experiments. Failure pressures for the poly(l-lactide) and poly(glycolide) specimens were not obtained because of the pressure limitations of the current apparatus. Instead, specimens showed no measurable change in length or surface texture after 4 hours at 9.5 MPa.

The glass transition pressures determined using EPR are relatively invariant with co-polymer composition, indicating the $CO_2$ interaction characteristics are similar with increasing glycolide composition. The same trend occurs for failure pressures of the amorphous polymers. However, the measured failure pressures always remained slightly higher than the glass transition pressure for the amorphous copolymers and poly(d,l-lactide) samples. This nearly uniform discrepancy is most likely caused by the difference in excitation frequency in the measurement technique. Kumler and Boyer show for various polymers that if one takes into account the change in excitation frequency (EPR=100 to 50 kHz, creep<<1 Hz) the transitions will agree. A similar adjustment in the magnitude of the EPR glass transition pressure is expected for the semi-crystalline homopolymers because of similar chemical composition. Regardless, the mechanical creep data indicate that the semi-crystalline poly(l-lactide) and poly(glycolide) homopolymers maintain sample shape far above the glass transition pressure determined from EPR spectrometry.

To understand the disagreement between the EPR and creep pressure transitions requires an understanding of the physical property the creep experiment measures. Typical creep experiments measure the change in sample length with time ($\Delta l/l_o t = \epsilon/t$). The present creep experiment measured or observed the change in creep rate due to solvent uptake. At small elongations, the stress ($\sigma$) experienced by the samples is constant. Therefore, any change in elongation rate must result from a decrease in Young's modulus ($E=\sigma/\epsilon$). Hence, the creep experiment presented herein effectively measures the change in Young's modulus with $CO_2$ uptake.

In the absence of compressed $CO_2$, the Young's moduli of the various polymers studied were on the same order of magnitude (Table 1) and all exhibit similar glass transition pressures. But the present experiments suggest that the semi-crystalline and amorphous polymer moduli diverge above the glass transition pressure. Janzen suggests that the behavior of Young's modulus above the $T_g$ yet below the melt temperature of a semi-crystalline polymer can be computed based on the embedding (or "self-consistent field") approach as reported in Janzen, *Polymer Engr. and Science*, 32(17):1242–1254 (1992). This predictive approach assumes no slip occurs at the interface between phases (amorphous phase, a, and crystalline phase, c). Further, the model assumes a simple spherical geometry for the dispersed phase to solve for material properties based on the volume fraction ($\phi$) and the properties of the two phases present (McGee & McCullough, *Polymer Composites*, 2(4):149–161 (1981); Janzen, supra).

The model consists of six equations (below) and eight independent variables (K, $K_a$, $K_c$, G, $G_a$, $G_c$, v, E). v can be found in Brandrup & Immergut, *Polymer Handbook*, 3d ed. (John Wiley & Sons, N.Y. 1989), and $G_a$ and $G_c$ are determined using amorphous and crystalline values of Young's modulus, E, respectively. A solution is obtained for each crystallinity volume fraction iteratively by initially guessing that the shear modulus, G, is equal to the amorphous value.

$$K = \frac{K_a K_c + A_k(\phi_a K_a + \phi_c K_c)}{A_k + \phi_c K_a + \phi_a K_c} \quad \text{Bulk Modulus} \quad \text{(I)}$$

$$A_k = 4G/3 \quad \text{(II)}$$

-continued $$G = \frac{G_a G_c + A_g(\phi_a G_a + \phi_c G_c)}{A_g + \phi_c G_a + \phi_a G_c} \quad \text{Shear Modulus} \quad (III)$$

$$A_g = \frac{G(9K + 8G)}{6(K + 2G)} \quad (IV)$$

$$v = \frac{3K + 2G}{2(G + 3K)} \quad \text{Poisson's Ratio} \quad (V)$$

$$E = 2(1 + v)G \quad \text{Young's Modulus} \quad (VI)$$

Figure 5:
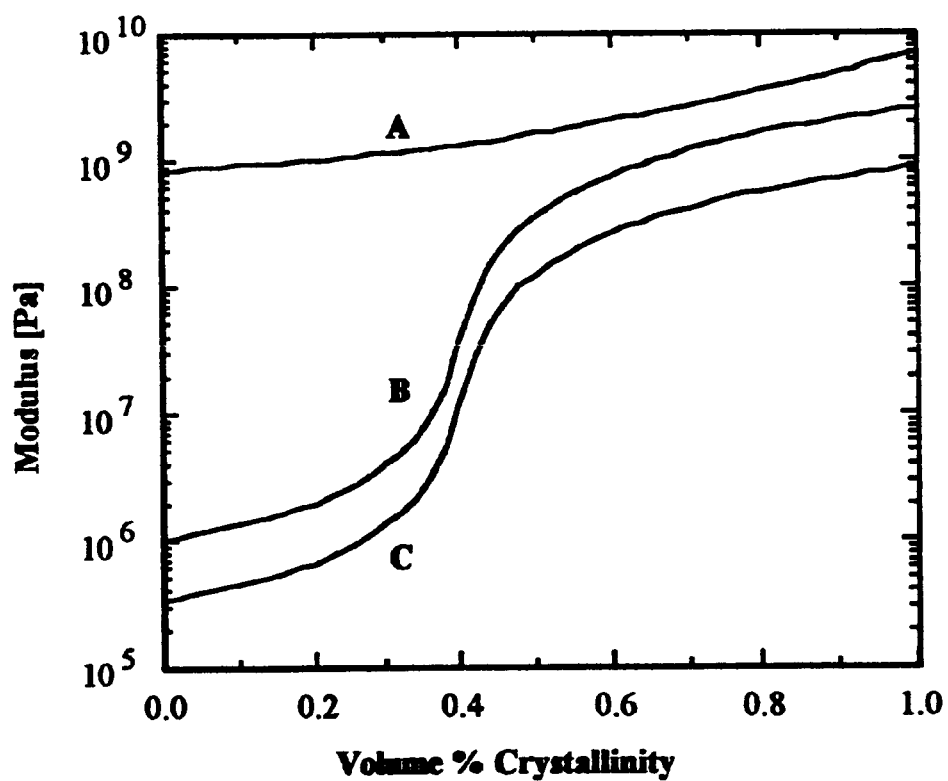
FIG. 5 graphically depicts self-consistent prediction of mechanical property variation with crystalline volume fraction for poly(lactide): (A) Bulk modulus, (B) Young's modulus, (C) Shear modulus.

FIG. 5 shows the predicted variation of mechanical properties in a semi-crystalline polymer. The amorphous and crystalline Young's modulus values used in the solution of the model were obtained from dynamic mechanical analyzer experiments conducted on poly(lactide) samples. The three orders of magnitude increase in Young's and shear modulus are typical for semi-crystalline polymers. Near 30% crystallinity by volume, the Young's modulus becomes twice that of the purely amorphous polymer and 20 times larger by 40% crystallinity. Slow cooling used in the formation of the polymer tensile specimen leads to near maximum crystallinity. Gilding and Reed published maximum crystallinity levels for lactide-glycolide copolymers in *Polymer*, 20:1459–1464 (1979). The homopolymers poly(glycolide) and poly(l-lactide) are semi-crystalline with crystallinity levels larger than 30%, while the poly(d,l-lactide) is amorphous. Copolymers containing d,l-lactide and glycolide remain amorphous until over 70% of the copolymer chain consist of glycolide blocks. As a result, only the semi-crystalline poly(l-lactide) and poly(glycolide) homopolymers are expected to retain Young modulus values 20 times larger than the amorphous polymer in the presence of high pressure $CO_2$. Larger Young's moduli or substantially lower creep rates in the semi-crystalline homopolymers are consistent with the inability to reach a failure pressure with these samples.

Attempts were made to process each of the various polymer samples using the PCA technique. Each polymer dissolved in $CH_2Cl_2$ (10 mg/ml) and injected into a compressed carbon dioxide environment using an ultrasonic nozzle. At 35° C. and 3.5 MPa, $CH_2Cl_2$ becomes highly soluble in $CO_2$, resulting in the rapid extraction of $CH_2Cl_2$ and precipitation of polymer microparticles. When operated in a continuous flow fashion (1 ml/min. Polymer solution; 25-ml/min. liquid $CO_2$) the micron sized particles are collected on a 0.2 µm filter down stream of the precipitation region.

Figure 6:
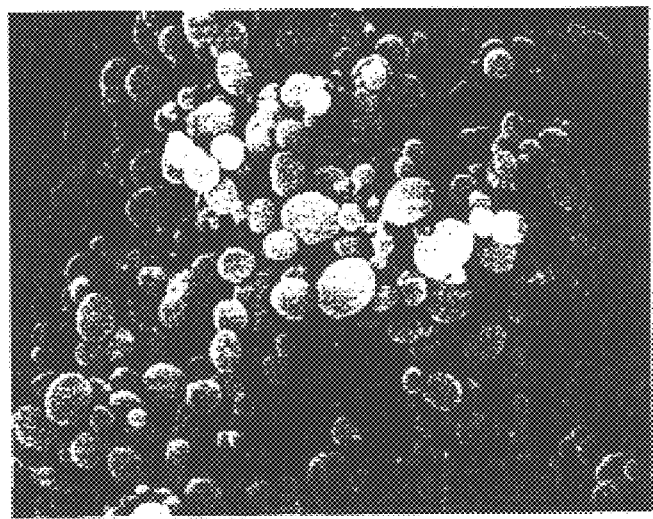
FIG. 6 is a SEM photomicrographs of (a) poly(l-lactide), (b) 50:50 poly(d,l-lactide-co-glycolide).
Figure 6:
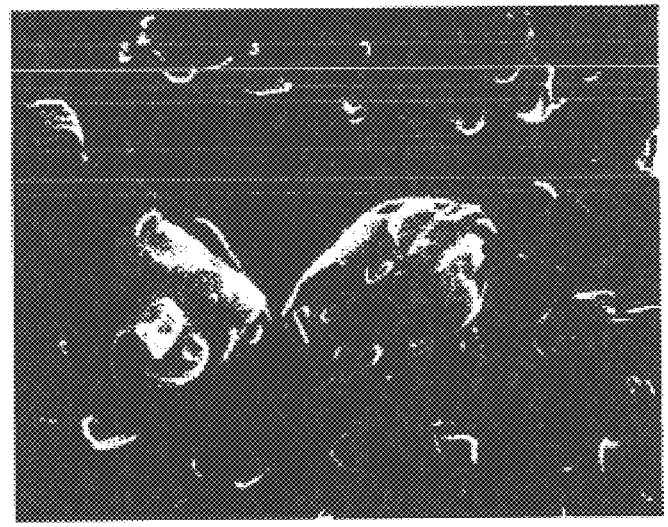

FIG. 6a shows a SEM photomicrograph of the semi-crystalline poly(l-lactide) particles formed by PCA. The light regions are the polymer particles, which are on the order of 1 to 2 µm in diameter. Tests using the same operating conditions, but dissolving poly(glycolide) in hexafluoroisopropanol (Strem Chemicals) yielded particle morphologies very similar to those seen in the poly(l-lactide) photomicrograph except for a slight decrease in particle diameter. Tests conducted on the amorphous poly(d,l-lactide) and poly(d,l-lactide-co-glycolide) yielded particle morphologies substantially different than those observed in the semi-crystalline polymers. FIG. 6b shows a SEM photomicrograph of 50:50 poly(d,l-lactide-co-glycolide) after PCA processing. The morphology presented in this photomicrograph is representative of the behavior exhibited by all amorphous polymers. The light region is continuous, indicating a thin film connecting regions of denser polymer resulting from severely agglomerated polymer particles.

X-ray diffraction and DSC crystallinity measurements of the poly(l-lactide) particles after processing show crystallinity levels near 25%. According to the embedding approach (FIG. 5), a crystallinity of 25% should not raise the Young's modulus substantially, but long polymer chains lead to entanglement between the amorphous and crystalline phase. The effects of phase entanglement are not captured in the spherical assumption of the theoretical model described. As entanglement increases, a smaller dispersed phase volume is required to affect bulk properties. As a result, a large change in Young's modulus at 25% crystallinity may not be a poor expectation from 100,000 molecular weight poly(l-lactide) molecules. Past literature indicates that the crystalline structure in a polymer system, such as poly(vinyl chloride), can begin to control a material's mechanical strength at crystallinities as low as 3% as reported in Walter, *J. Polymer Sci.*, 13:207 (1954) and Koleske & Wartman, *Poly(vinyl chloride)*, pp. 67–69 (Gordon & Breach Science, N.Y. 1969). In addition, the x-ray diffraction and DSC measurements make no distinction between surface layer and bulk crystallinity. If the majority of the crystalline domains are located at the surface of the particle, the local crystallinity may be quite large, resulting in a strong exterior shell.

Figure 7:
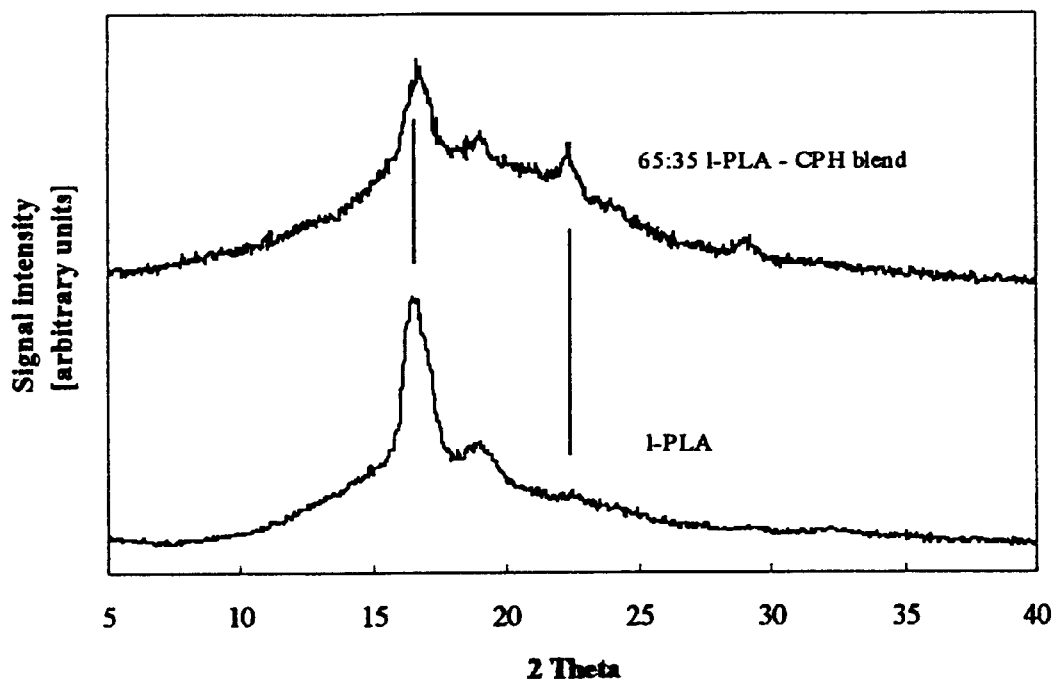
FIG. 7 are x-ray powder diffraction scans of polymer microparticles formed by PCA: poly(l-lactide), 60:30 blend of poly(l-lactide) and CPH.

Several attempts were made to determine a critical crystallinity for poly(l-lactide), below which particle shape could not be maintained during PCA processing. Crystallinity levels in the particles were lowered through the addition of impurities. The addition of $CO_2$ insoluble molecules with a molecular structure different than l-lactide in the $CH_2Cl_2$-polymer solution may limit the crystalline levels obtained during PCA. Further, varying the volume fraction of impurity should allow manipulation of the resulting processed particle crystallinity. Impurities such as semi-crystalline linear 1,6 bis (carboxyphenoxy)hexane (CPH) seemed to have little effect on the particle morphology. A x-ray diffraction scan (FIG. 7) revealed that the resulting particles have partially phase separated into different crystalline regions that help maintain the polymers mechanical strength. The first peak in FIG. 7 represents crystallized poly(l-lactide), whereas the second dominant peak represents crystallized CPH.

Figure 8:
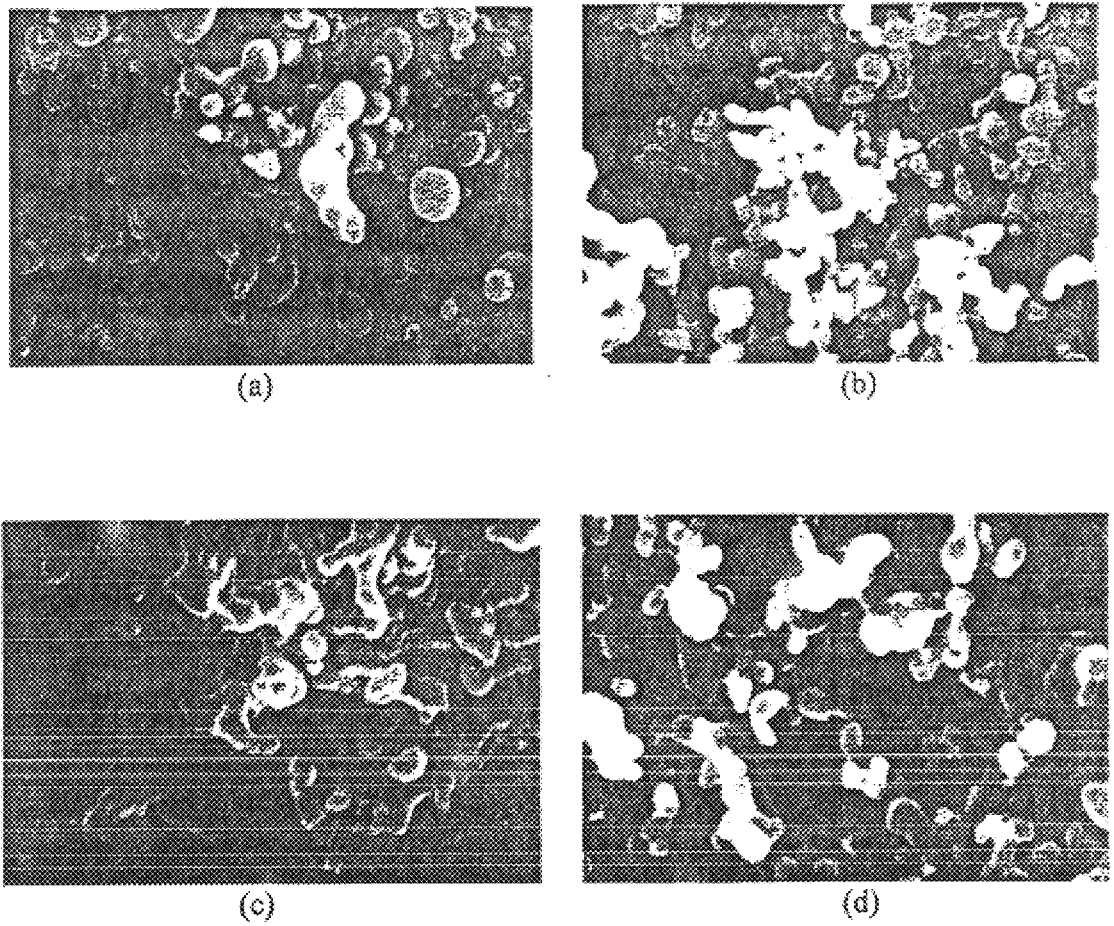
FIG. 8 are SEM photomicrographs of polymer microparticles formed using precipitation with a compressed antisolvent at 8.5 MPa, 35° C., solvent flow rate=1 ml/min., $CO_2$ flow rate=25 ml/min., and an original polymer to solution leading of 10 mg/ml: (a) 100% poly(l-lactide), 26% crystalline; (b) 80% poly(l-lactide)-20% poly(d,l-lactide) blend by mass, 19% crystalline; (c) 60% poly(l-lactide)-40% poly (d,l-lactide) blend by mass, 12% crystalline; (d) 85:15 poly(l-lactide-co-glycolide), 15% crystalline.

Success in lowering the particle crystallinity was obtained through the addition of amorphous poly(d,l-lactide). FIG. 8 shows the resulting SEM micrographs from PCA processed poly(l-lactide) particles with 0, 20, and 40% by mass poly(d,l-lactide) (26, 19 and 12% crystallinity, respectively). As particle crystallinity decreases, agglomeration becomes more prevalent, dominating morphology near 12% crystallinity. To verify this trend was not a result of impurities phases separating and depositing on the particle surface, 85:15 poly(l-lactide-co-glycolide), a block co-polymer with a maximum crystallinity between 15 and 20% (McGee, supra.), was processed. In FIG. 8, the poly(l-lactide-co-glycolide), 15% crystalline, particles are partially agglomerated. The extent of particle agglomeration exhibited by the poly(l-lactide-co-glycolide) particles agrees with the trend established using particles formed through the addition of impurities, displaying a morphology between the 12 and 19% crystalline particles.

It is believed that the critical crystallinity required for poly(lactide) or poly(glycolide) to maintain particle morphology during PCA conditions above their glass transition is near 12%. In the PCA process, crystallinity evolves with time as organic solvent is removed from the polymer. The final crystallinity measured in the study may not be the actual particle crystallinity at the time of impact with adjacent particles. As a result, the actual critical crystallinity to maintain particle morphology may be less than 12%. In addition, this crystallinity value will vary from polymer to polymer.

Absorption of compressed $CO_2$ into a polymer can suppress the glass transition temperature below the operating temperature of a PCA system. This $T_g$ suppression results from interaction characteristics between the pure polymers and the $CO_2$ diluent (Condo et al., *Macromolecules*, 25(23):6119–6127 (1992); Kalosiros & Paulaitis, *Chem. Engr. Science*, 49(5):659–668 (1994)). However, polymers can retain particle morphology above their $T_g$ because of moderate crystalline volume fractions that slow the relaxation of mechanical strength causing a creep rate low enough to limit agglomeration. As a result, certain semi-crystalline polymers retain microparticle morphology during PCA conditions above their glass transition temperature.

Although the invention has been described with reference to the presently disclosed embodiments, it should be understood that various modifications can be made without departing from the spirit or scope of the invention. Accordingly, the invention is limited only by the following claims.

We claim:

1. A method for making semi-crystalline copolymeric microparticles in a precipitation by compressed antisolvent (PCA) process, comprising the steps of:
   (a) providing a semi-crystalline copolymer; and
   (b) exposing said semi-crystalline copolymer to a compressed antisolvent at a temperature of about 35° C. and pressure of 3 to 9.5 MPa, to form said semi-crystalline copolymenric microparticles.

2. The method of claim 1, wherein said copolymer is poly(lactide-co-glycolide) copolymer.

3. The method of claim 1, wherein the antisolvent is carbon dioxide.

4. The method of claim 3, wherein the antisolvent is supercritical or liquid carbon dioxide.

5. The method of claim 1, wherein the copolymer has a critical crystallinity of about 10% to about 15%.

6. The method of claim 2, wherein the copolymer has a critical crystallinity of about 12%.

7. The method of claim 1, wherein components of the copolymer are in a ratio from 100:0 to 0:100.

8. The method of claim 2, wherein the copolymer is in a ratio from about 50:50 to about 30:70 of poly(lactide):poly(glycolide).

* * * * *